(12) United States Patent  (10) Patent No.: US 7,547,278 B2
Miyazaki et al.  (45) Date of Patent: Jun. 16, 2009

(54) TELE-CARE MONITORING DEVICE

(75) Inventors: Jinsei Miyazaki, Fort Lee, NJ (US); Kenji Iwano, Katano (JP); Kazutoshi Nagai, Ikoma (JP); Toshiyuki Tanaka, Yamatokohriyama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 431 days.

(21) Appl. No.: 10/330,928

(22) Filed: Dec. 27, 2002

(65) Prior Publication Data

US 2004/0127775 A1 Jul. 1, 2004

(51) Int. Cl.
*A61B 5/00* (2006.01)
(52) U.S. Cl. .................. 600/300; 434/262; 128/920
(58) Field of Classification Search ......... 600/300–301; 128/920, 903–904; 340/573; 348/17; 379/106.02; 705/2–4; 345/573.1
See application file for complete search history.

(56) References Cited

U.S. PATENT DOCUMENTS

| | | | |
|---|---|---|---|
| 5,801,755 A * | 9/1998 | Echerer | 348/14.01 |
| 5,997,476 A * | 12/1999 | Brown | 600/300 |
| 6,014,432 A * | 1/2000 | Modney | 379/106.02 |
| 6,080,106 A * | 6/2000 | Lloyd et al. | 600/300 |
| 6,290,646 B1 | 9/2001 | Cosentino et al. | |
| 6,402,691 B1 * | 6/2002 | Peddicord et al. | 600/300 |
| 6,478,736 B1 * | 11/2002 | Mault | 600/300 |
| 6,589,169 B1 * | 7/2003 | Surwit et al. | 600/300 |
| 6,620,106 B2 | 9/2003 | Mault | |

OTHER PUBLICATIONS

Microsoft Computer dictionary, Microsoft Press, 5th Edition, p. 399.*
http://medicalmailorder.com/stethoscopes_other.html—Website for stethoscopes—Physicianequipment.com, pp. 1-14.
http://medicalmailorder.com/electrocardiographs.html—Website for Electrocardiographs, pp. 1-4.

* cited by examiner

*Primary Examiner*—Max Hindenburg
*Assistant Examiner*—Michael Astorino
(74) *Attorney, Agent, or Firm*—Harness, Dickey & Pierce, PLC

(57) ABSTRACT

A scalable tele-care monitoring device has a plurality of physiological sensors adapted to collect patient physiological data. The device also has an interface adapted to connect with a personal computer, and an expansion module adapted to communicate patient physiological data to the personal computer via the interface. In further aspects, the device has an output adapted to communicate the patient physiological data over a communications network when the device is not interfaced with the personal computer.

34 Claims, 6 Drawing Sheets

TELE-CARE MONITORING DEVICE

FIELD OF THE INVENTION

The present invention generally relates to tele-care monitoring systems, methods, and devices, and particularly relates to a scalable tele-care monitoring device capable of interfacing with a patient's personal computer, thereby achieving expanded functionality.

BACKGROUND OF THE INVENTION

Today's tele-care monitoring devices are often prohibitively expensive and/or limited in-functionality without the ability to interface with one another in a complementary fashion. For example, a tele-care monitoring device is taught in U.S. Pat. No. 6,402,691, entitled In-Home Patient Monitoring System, and issued to Peddicord et al. This device is capable of collecting patient physiological data in the form of a blood pressure reading, temperature reading, pulse oximeter reading, and/or weight reading, and communicating the data to a clinician over a communications network. This device, however, does not have the ability to implement health care monitoring equipment to collect and transmit large amounts of audio data in digital form, such as with an electrocardiograph and/or stethoscope, nor does it provide teleconferencing capability.

Some commercially available stethoscopes and electrocardiographs are capable of interfacing with a patient's personal computer (PC) and/or handheld device via an audio input and complementary software, thereby creating a wave file recording user physiological data. Examples of such equipment include the Meditron Sensor-Based Stethoscope System and the IQMark Digital ECG.

A maker of tele-care monitoring systems and devices is presented with competing needs of less critical patients who do not require collection and telecommunication of digital audio data, and more critical patients who require collection and telecommunication of both digital readings and digital audio data. For example, requiring acquisition of a PC or monitoring device capable of collecting and communicating audio data presents increased expense for less critical patients and/or their care-givers. Also, requiring purchase of a dedicated device for digital readings presents an inconvenience for the more critical patients and/or caregivers based on the need to undergo separate data collection and communication procedures between devices. Further, caregivers of patients and/or patients transitioning from less critical status to more critical status may be faced with the need to either purchase an entirely new device capable of collecting and communicating digital readings and digital audio data, or undergo separate collection/communication procedures with separate devices.

The need remains for a tele-care monitoring device that is designed to be inexpensive for less critical patients, and is expandable for more critical patients without requiring purchase of a separate device having functionality that is redundant with functionality of a device already owned. The need further remains for a monitoring device that is capable of expanding by integrating with a PC already owned by a patient or caregiver, so that less additional expense is incurred. Finally, the need remains for an inexpensive monitoring device that is capable of integrating with a PC to provide teleconferencing capability, thereby permitting patient monitoring procedures to be conducted under long-distance supervision of a clinician. The present invention fulfills the aforementioned needs.

SUMMARY OF THE INVENTION

According to the present invention, a tele-care monitoring device has a plurality of physiological sensors adapted to collect patient physiological data. The device also has an interface adapted to connect with a personal computer, and an expansion module adapted to communicate patient physiological data to the personal computer via the interface. In further aspects, the device has an output adapted to communicate the patient physiological data over a communications network when the device is not interfaced with the personal computer.

It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
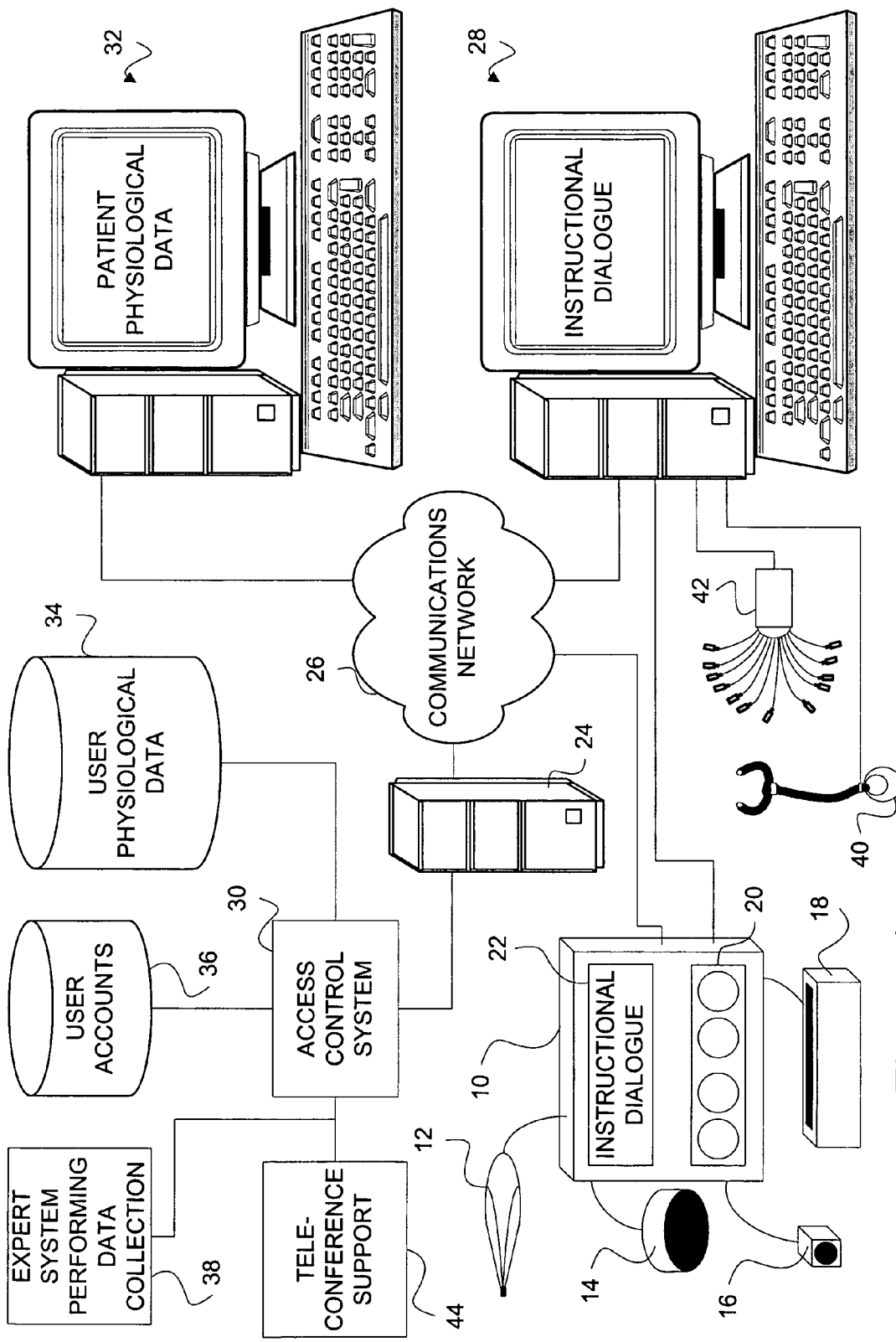
FIG. 1 is a partial perspective block diagram depicting a scalable tele-care monitoring system according to the present invention.

According to the present invention and as illustrated in FIG. 1, a scalable tele-care monitoring system includes scalable tele-care monitoring device 10, which is operable to obtain patient physiological data via a plurality of sensors, such as digital thermometer 12, blood pressure gauge 14, pulse oximeter 16, and scale 18. Additional or alternative digital sensors include a pedometer, a blood glucose meter, a spirometer, and/or a sensor for measuring international normalized ratio of prothrombin time (PT/INR). It also has a user interface, including user input devices 20 allowing a user to make selections, and a user output device 22 communicating information to the user. Preferably, user input devices 20 have 10 keys for input of numeric data, and device 10 can accept numeric input. This capability allows a user to preferably use their own familiar sensor that is not supported by device 10. It further has an output (not shown) adapted to communicate collected patient physiological data to acquisition server 24 over communications network 26. Finally, it has an interface (not shown) for connecting to PC 28, and adapted to communicate the patient physiological data to PC 28.

Acquisition server 24 has access control system 30 adapted to control access of device 10, PC 28, and clinician computer 32 to services of server 24. For example, access control system 30 is adapted to store user physiological data received from device 10 and/or PC 28 in data store 34 in accordance with user accounts information 36; it also allows a clinician to access data store 34 and retrieve the user physiological data. Server 24 is further adapted to provide expert system 38 to PC 28, thus enabling PC 28 to guide a user through a physiological data collection process that includes using PC 28 to obtain physiological data via device 10, and affecting communication of the physiological data from PC 28 to acquisition server 24.

According to various embodiments for use with the Internet, system 38 is provided as a website with appropriate servlets, applets, and/or plugins, as a website with downloadable software, and/or on one or more data storage components provided as complimentary software to device 10. If system 38 is at least partially installed on PC 28, then it can be configured to automatically launch upon detection of connection with device 10. PC 28 thus tracks whether a device is connected through a USB port provided to PC 28 and, if detecting connection of device 10, launches software according to predetermined criteria.

Principally, system 38 provides an instructional dialogue guiding the user through the data collection process, using sensors provided to device 10, and using additional sensors, such as stethoscope 40 and electrocardiograph 42, provided to PC 28. System 38 further provides additional functions, such as graphic display of data stored in device 10, on PC 28, and/or in data store 34. It also offers more complex questionnaires than device 10, even with respect to performing diagnosis with sensors provided to device 10. It provides more advanced instruction as well, especially in relation to use of voice and pictures to provide instruction. It additionally offers web browsing capability that provides medical related information and/or questionnaires, wherein the information and/or questionnaires can be selected for and communicated to the user by the expert system. Thus, the system of the present invention capitalizes on PC 28's ability to collect and store large amounts of audio data and to interface with device 10, thereby collecting more types of data in one step and storing it on line in data store 34 for evaluation by a clinician. It also capitalizes on the ability to provide superior instructions in the form of video demonstrations and/or video conference-based supervision. Further embodiments also permit device 10 to have limited web browsing capability for acquiring questionnaires over the communications network that are provided to web browsers via expert system 38.

The system of the present invention preferably supports teleconferencing between a clinician and a user via PC 28 using a separate line to support video conferencing capability. Thus, PC 28 and computer 32 preferably have teleconference software installed as well as cameras, head phones, and H324 compliance modems, and are directly connected by telephone line via modem on each side. In this case, the communication protocol is raw data communication (H324) and not Internet Protocol (IP).

In an alternative embodiment, IP format can be used for video and/or audio teleconferencing. For example, server 24 can provide teleconferencing support by serving as an intermediary of teleconferencing information. Alternatively, peer to peer communication functionality in an IP format can be provided to PC 28 and computer 32, either as a download or as software provided on a data storage medium. As a result, a user and/or clinician can initiate a call by clicking on an icon on the respective computer's desktop, and/or select a function in a program running on the computer. As a result, a user of device 10 can call for assistance via PC 28 by clicking on an icon provided on a website running on server 44, thereby initiating a teleconferencing call with computer 32; a clinician reviewing patient physiological data can similarly initiate a teleconference. The clinician, in turn, obtains access to the user physiological data via computer 32 using a web browser.

Figure 2:
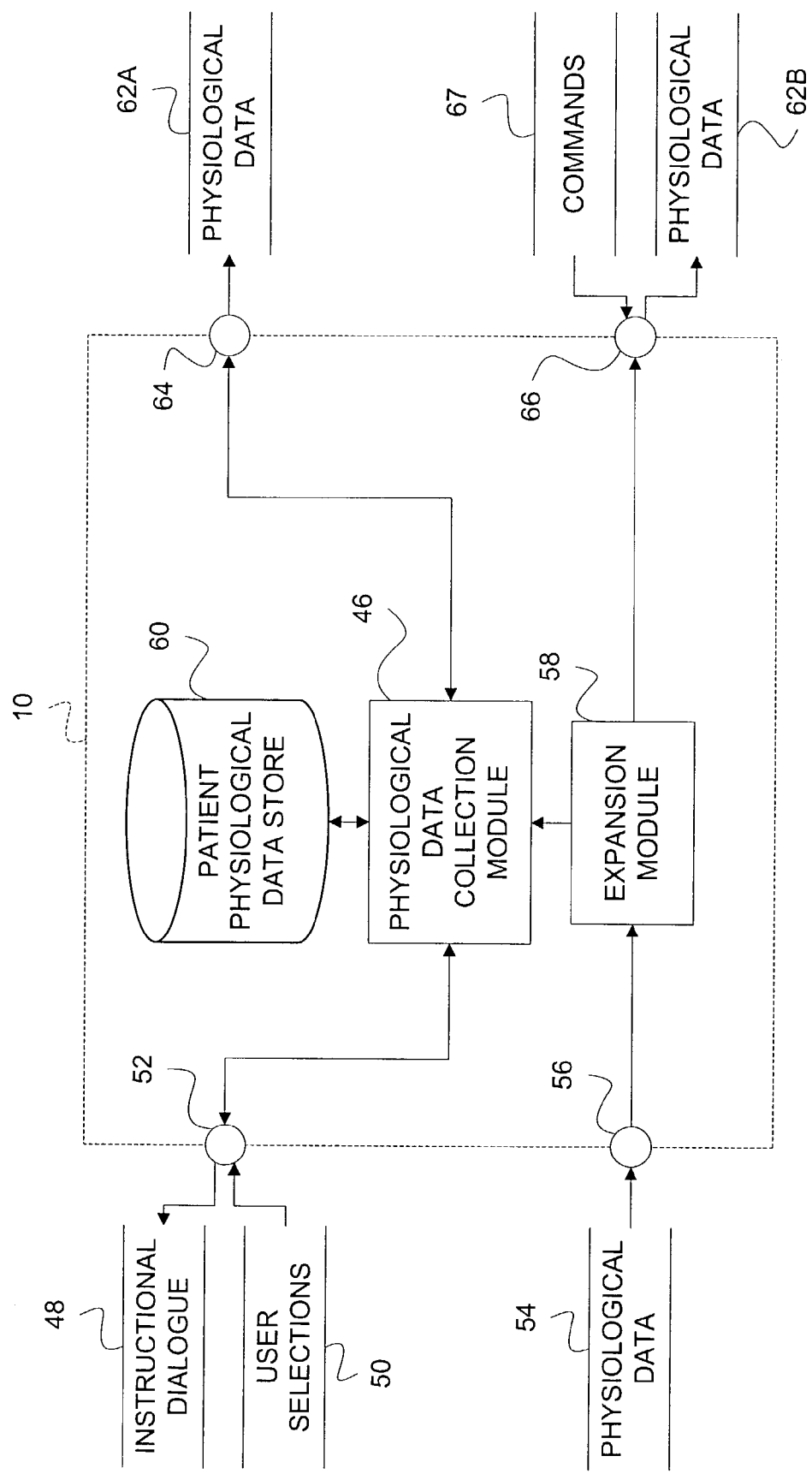
FIG. 2 is a block diagram depicting a scalable tele-care monitoring device according to the present invention.

FIG. 2 illustrates device 10, which has physiological data collection module 46 adapted to generate instructional dialogue 48 guiding a user through the data collection process. Instructional dialogue 48 is generated in response to user selections 50 communicated to module 46 via user interface 52, and instructional dialogue 48 is also communicated to the user via user interface 52. In normal operation, patient physiological data 54 is obtained via plurality of sensors 56, and routed through expansion module 58, which selects an active sensor in response to commands from module 46, to module 46, which stores collected data in data store 60. Module 46 then sends collected data 62A over a communications network (not shown) via output 64. Device 10 further has interface 66, which is adapted to connect to a PC (not shown). Expansion module 58 continuously monitors interface 66, and, upon detecting connection to a PC via interface 66, expansion module 58 causes module 46 to cease normal operation, and begins routing collected physiological data 62B to the PC via interface 66. Module 58 further selects an active sensor in response to commands 67 from the PC. In the preferred embodiment, physiological data 54 is also routed to module 46 for storage in data store 60, so that a record is maintained.

Figure 3:
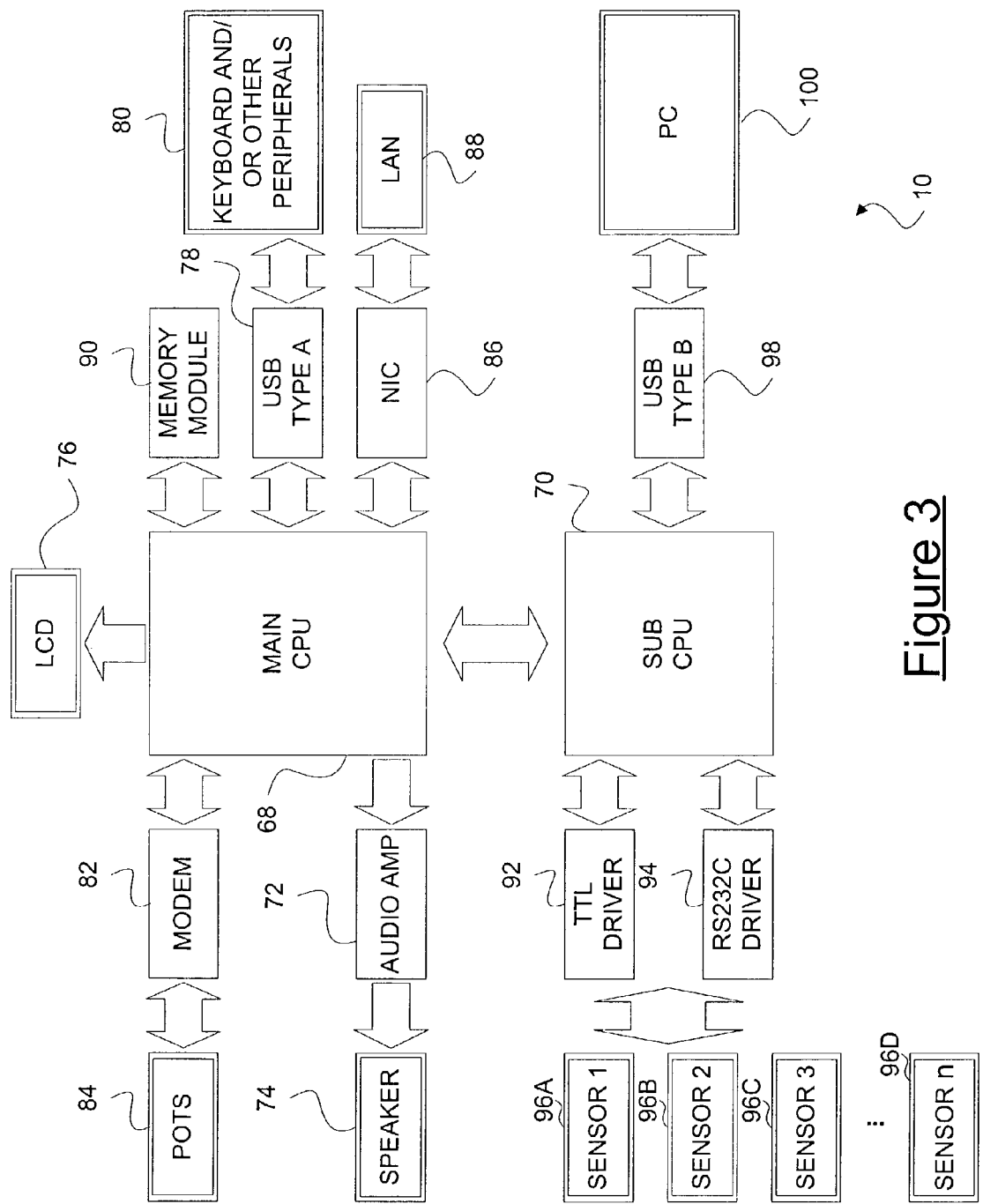
FIG. 3 is a block diagram depicting the preferred embodiment of a scalable tele-care monitoring device according to the present invention.

The preferred embodiment of device 10 is illustrated in FIG. 3. For example, device 10 has a main central processing unit 68 serving as the data collection module, and a subordinate central processing unit 70 serving as the expansion module. Also, audio amp 72 and speaker 74 serve as one user output component, while liquid crystal display 76 serves as another user output component. Further, Type A USB port 78 and peripheral input devices 80 serve as an input component, and the aforementioned components combine to form a user interface. Still further, device 10 has a modem 82 connecting to plain old telephony service 84, and network interface card 86 connecting to line access network 88. As a result, device 10 has an output capable of connecting to an administration server in a variety of ways. Yet further, device 10 has a memory module 90, such as a disc, hard drive and/or flash memory, storing patient physiological data. Even further, device 10 has transistor-transistor logic driver 92 and/or RS232C driver 94 connecting to plurality of sensors 96A-96D and serving as a sensory input. Finally, Type B USB port 98 connects to PC 100, thus serving as an interface.

Figure 4:
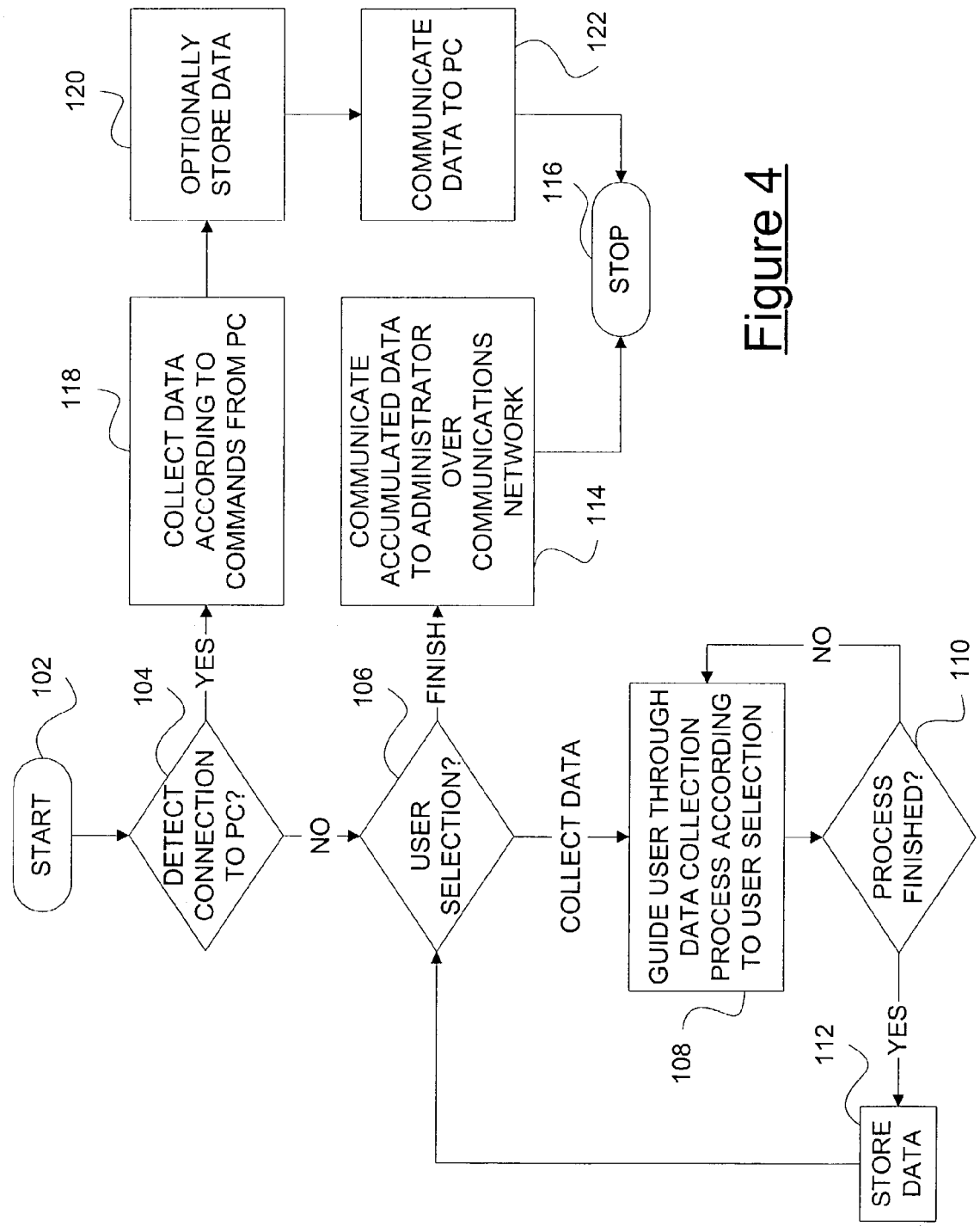
FIG. 4 is a flow diagram depicting a method of operation for a tele-care monitoring device according to the present invention.

A method of operation for a scalable tele-care monitoring device is illustrated in FIG. 4. Beginning at 102, the method includes detecting connection to a PC at 104, and switching between a normal and passive mode based on whether the device is connected to the PC. This operation can be performed by a control system that is always active and running in the background, or a switch that causes a different set of circuitry to be engaged when a particular connection is made. The device operates in normal mode when the PC is not connected, and in passive mode when the PC is connected.

In normal mode, the device operates in response to user selections as at 106 that the user inputs to the device through a user interface provided to the device. Thus, the device guides the user through the data collection process at 108 depending on selections made by the user. For example, when the user selects to collect data with a particular type of sensor, the device activates the sensor, deactivates any other active sensors, and issues text and/or voice-based instructions for applying the sensor to the patient, who may be the user. Alternatively, the device can instruct the user to toggle a switching mechanism provided to the device for activating a sensor in favor of other sensors. Then, when the data collection process has been finished as at 110, the collected data is stored in the device at 112 and the user is prompted for another selection at 106. The user can then select another data collection process, or select to finish and transmit the collected data. In the latter case, the accumulated data is communicated at 114 to the administration server over a communications network, such as the Internet, and the method ends at 116.

In passive mode, the device is adapted to display its state change on an active display provided to the device, and to retain its sensory function, but to no longer provide instructions to the user. The assumption made in operation of the device is that the user receives all instructions from the connected PC, which are superior due to their ability to provide video instructions. Thus, the device obtains sensory data at 118 in response to instructions from the PC, not selections from the user, and activates a sensor in favor of other sensors in response to those instructions. An instruction from the expansion module to the data collection module causes it to merely to optionally store data at 120, and the instruction identifies the type of data being stored. Alternatively, the device simply routes any sensory input to the PC and allows the PC to instruct the user to toggle a switching mechanism provided to the device that activates one sensor in favor of other sensors. Such a switching mechanism can also serve to identify the data for optional storage in a data store on the device at 120. In either case, the device communicates the sensed data at 122 to the PC as it is collected, and the method ends at 116.

Figure 5:
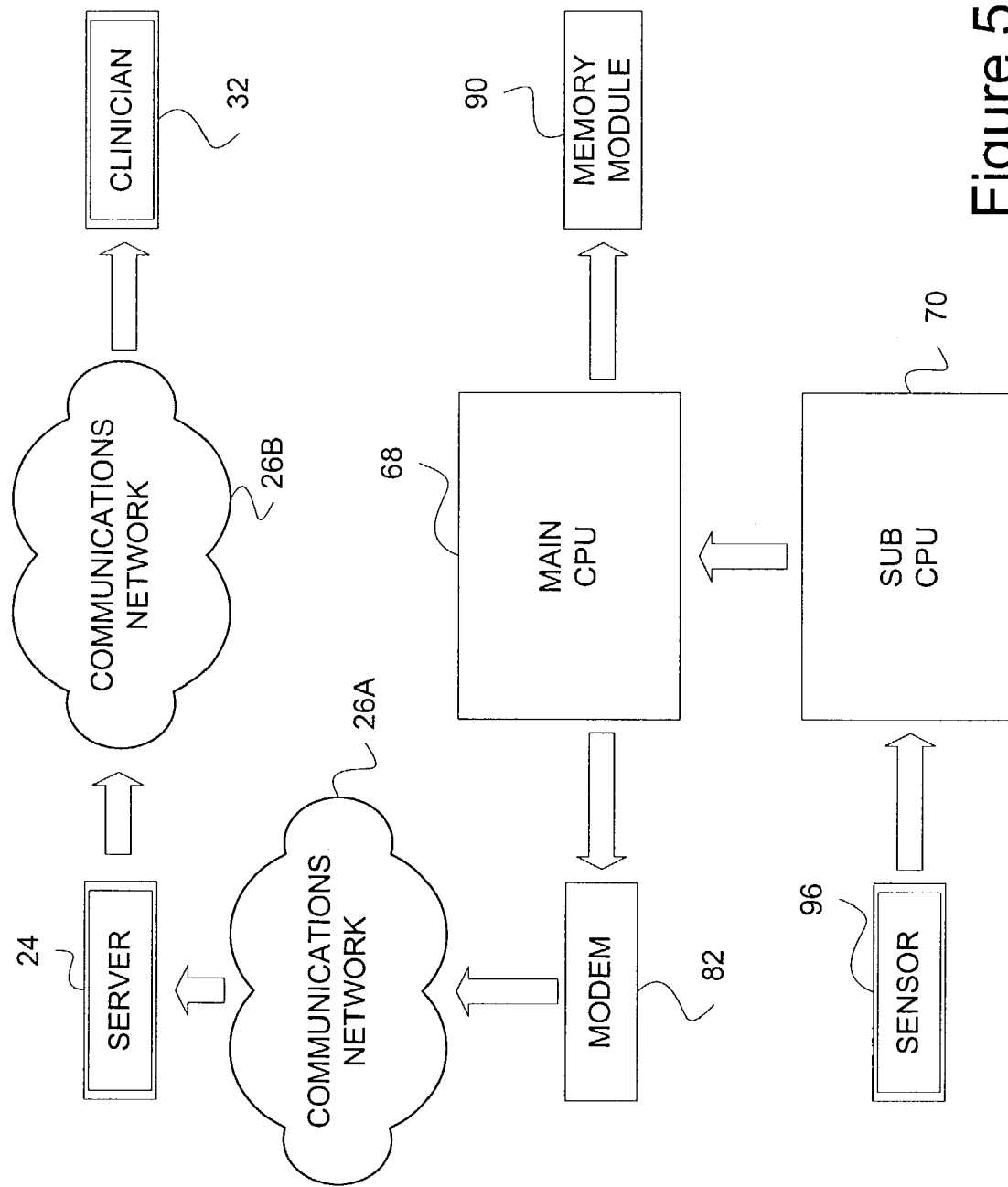
FIG. 5 is a block and flow diagram depicting a first route for communication of patient physiological data according to the present invention.
Figure 6:
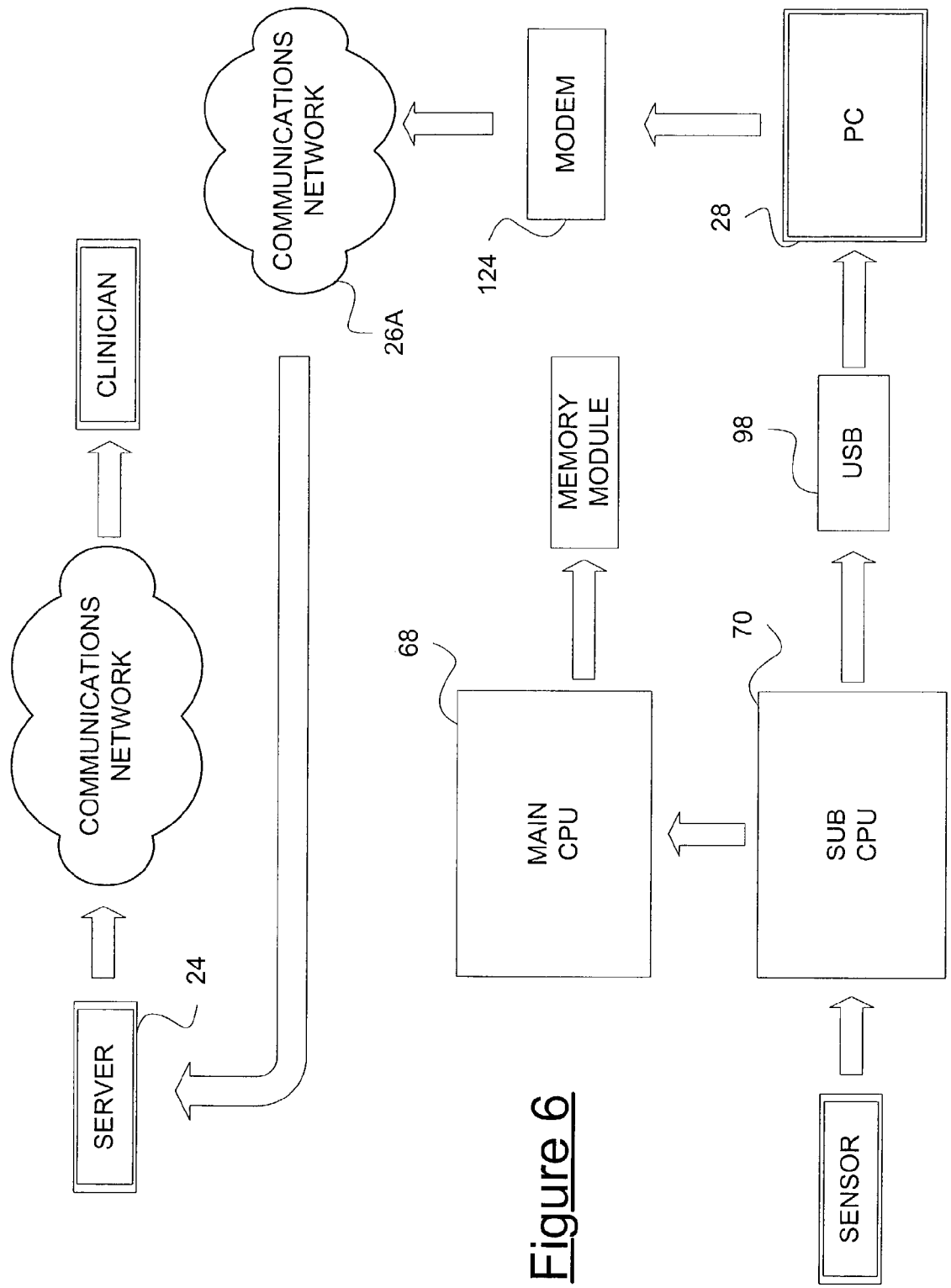
FIG. 6 is a block and flow diagram depicting a second route for communication of patient physiological data according to the present invention.

Two routes of communication for obtained data according to the present invention are illustrated in FIGS. 5 and 6. These routes differ in that, FIG. 5 illustrates a route for communication of obtained data from the sensor to the clinician when the scalable device is operating in normal mode, while FIG. 6 illustrates a route of communication of obtained data from the sensor to the clinician when the scalable device is operating in passive mode due to connection with a PC. For example, the route of communication illustrated in FIG. 5 proceeds from sensor 96 to subordinate central processing unit 70, and to main central processing unit 68. Main central processing unit 68 optionally splits the route by optionally storing the obtained data in memory module 90, in addition to outputting the data via an output device, such as modem 82 to communications network 26A. The data is routed to acquisition server 24, which, in turn, routes the data through communications network 26B to the clinician via clinician computer 32. Further, the route of communication illustrated in FIG. 6 differs from that of FIG. 5 in that main central processing unit 68 (FIG. 6) does not output the data to communications network 26A. Instead, subordinate central processing unit communicates the data to PC 28 via USB port 98, and PC 28 outputs the data to communications network via its own modem 124, causing it to be routed to acquisition server 24.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A tele-care monitoring device, comprising:
   a plurality of physiological sensors that collect patient physiological data;
   a tele-care monitoring device adapted to receive patient physiological data from the plurality of physiological sensors and having an interface configured to connect to a personal computer, the monitoring device further including:
   a data collection module residing on the monitoring device that communicates the patient physiological data via an output over a wired communications network during normal operation; and
   an expansion module in data communication with the data collection module and residing on the monitoring device, the expansion module monitors the interface and, upon detecting a connection via the interface to a personal computer, ceases communication of the patient physiological data over the communications network by the data collection module and initiates communication of the patient physiological data over the interface to the personal computer.

2. The device of claim 1, further comprising a data store adapted to store the patient physiological data.

3. The device of claim 1 wherein said data collection module generates an instructional dialogue guiding a user through said normal operation; and wherein said tele-care monitoring device further comprises a user interface communicating the instructional dialogue to the user.

4. The tele-care monitoring system of claim 3 wherein the data collection module ceases to provide instructional dialogue to the user upon detecting the connection via the interface to the personal computer.

5. The device of claim 1 wherein said data collection module generates an instructional dialogue guiding a user through said normal operation in response to a user selection relating to a type of physiological sensor; and wherein said tale-care monitoring device further comprises a user interface communicating the user selection to the data collection module.

6. The device of claim 1, further comprising
   a user interface has an input mechanism permitting a user to input numerical data in place of a sensor reading.

7. The device of claim 1, wherein said plurality of physiological sensors includes a blood pressure gauge.

8. The device of claim 1, wherein said plurality of physiological sensors includes a pulse oximeter.

9. The device of claim 1, wherein said plurality of physiological sensors includes a thermometer.

10. The device of claim 1, wherein said plurality of physiological sensors includes a scale.

11. The device of claim 1, wherein said plurality of physiological sensors includes a blood glucose meter.

12. The device of claim 1, wherein said plurality of physiological sensors includes a sensor for measuring international normalized ratio of prothrombin time.

13. The device of claim 1, wherein said plurality of physiological sensors includes a spirometer.

14. The device of claim 1, wherein said plurality of physiological sensors includes a pedometer.

15. The tele-care monitoring system of claim 1 wherein the expansion module ceases communication of the patient physiological data over the interface and resumes communicating the patient physiological data via the output over the communication network upon detecting that the connection via the interface to the personal computer is terminated.

16. The tele-care monitoring system of claim 1 wherein the expansion module receives user instructions from the personal computer when the connection to the personal computer is detected.

17. The tele-care monitoring system of claim 1 wherein the user instruction received from the personal computer relates to a selection of a type of physiological sensor and the data collection module is operable to activate the selected physiological sensor in response to the user instruction.

18. A tele-care monitoring system, comprising:
an acquisition server connected to a communications network and adapted to receive patient physiological data over the wired communications network, the acquisition server stores the patient physiological data and communicates the patient physiological data to a clinician computer over the communications network;
a tele-care monitoring device operably connectable to the wired communications network and having an interface for connecting with a personal computer operably connected to the wired communications network, the monitoring device further includes
a data collection module residing in the monitoring device and communicating the patient physiological data over the communications network in a normal operation mode,
an expansion module residing on the monitoring device that detects a connection via the interface to a personal computer, the expansion module communicates the patient physiological data in a passive mode via the interface to a personal computer and discontinues communicating the patient physiological data over the communication network when a connection exists via the interface to the personal computer; and
an expert system guiding a user under said passive operation to obtain physiological data via said device, and affecting communication of the physiological data from the personal computer to the acquisition server.

19. The system of claim 18, wherein monitoring device guides the user through a physiological data collection process via monitoring device only under normal operation.

20. The system of claim 18, wherein said expert system includes patient physiological data corresponding to digital audio data, and is configured to affect communication of the digital audio data to the acquisition server over the wired communications network.

21. The system of claim 18, wherein the personal computer has an electrocardiograph, and said expert system employs the electrocardiograph to collect patient physiological data.

22. The system of claim 18, wherein the personal computer has a stethoscope, and said expert system employs the stethoscope to collect patient physiological data.

23. The system of claim 18, wherein said monitoring device further includes a pulse oximeter, and said expert system employs the pulse oximeter to collect patient physiological data.

24. The system of claim 18, wherein said monitoring device: further includes a blood pressure gauge, and said expert system employs the blood pressure gauge to collect patient physiological data.

25. The system of claim 18, wherein said monitoring device further includes a thermometer, and said expert system employs the thermometer to collect patient physiological data.

26. The system of claim 18, wherein said monitoring device further includes a scale, and said expert system employs the scale to collect patient physiological data.

27. The system of claim 18, wherein said monitoring device further includes a spirometer, and said expert system employs the spirometer to collect patient physiological data.

28. The system of claim 18, wherein said monitoring further includes a pedometer, and said expert system employs the pedometer to collect patient physiological data.

29. The system of claim 18, wherein said monitoring device further includes a blood glucose meter, and said expert system employs the blood glucose meter to collect patient physiological data.

30. The system of claim 18, wherein said monitoring device further includes a sensor for measuring international normalized ratio of prothrombin time, and said expert system employs the sensor for measuring international normalized ratio of prothrombin time to collect patient physiological data.

31. The system of claim 18, wherein said acquisition server supports teleconferencing capability between the clinician computer and the personal computer via the wired communications network.

32. The system of claim 18, wherein the personal computer and the clinician computer are equipped with video conferencing equipment, thereby providing mutual communication between the clinician and a user.

33. The system of claim 18, wherein said expert system includes online via web browsing capability, and provides questionnaires to the user, and said monitoring device further includes a web browsing capability.

34. The system of claim 18, wherein said expert system is provided as installable software to the personal computer, and provides questionnaires to a user via the personal computer.

* * * * *

UNITED STATES PATENT AND TRADEMARK OFFICE
CERTIFICATE OF CORRECTION

PATENT NO. : 7,547,278 B2
APPLICATION NO. : 10/330928
DATED : December 27, 2002
INVENTOR(S) : Jinsei Miyazaki et al.

It is certified that error appears in the above-identified patent and that said Letters Patent is hereby corrected as shown below:

Column 6, Line 37, Claim 5:
 "tale-care" should be "tele-care"
Column 8, Line 9, Claim 24:
 Remove ":" after the word "device"
Column 8, Line 22, Claim 28:
 After "monitoring" insert --device--

Signed and Sealed this

Sixth Day of October, 2009

David J. Kappos
*Director of the United States Patent and Trademark Office*